US008637073B2

(12) United States Patent
Reidenberg et al.

(10) Patent No.: US 8,637,073 B2
(45) Date of Patent: Jan. 28, 2014

(54) TREATMENT OF DEPENDENCE WITHDRAWAL

(75) Inventors: Bruce E. Reidenberg, Rye, NY (US); Daniel A. Spyker, Burlingame, CA (US)

(73) Assignee: Purdue Pharma L.P., Stamford, CT (US)

( * ) Notice: Subject to any disclaimer, the term of this patent is extended or adjusted under 35 U.S.C. 154(b) by 1763 days.

(21) Appl. No.: 10/566,121

(22) PCT Filed: Jul. 26, 2004

(86) PCT No.: PCT/US2004/024010
§ 371 (c)(1),
(2), (4) Date: Jan. 25, 2006

(87) PCT Pub. No.: WO2005/011579
PCT Pub. Date: Feb. 10, 2005

(65) Prior Publication Data
US 2006/0240085 A1    Oct. 26, 2006

Related U.S. Application Data

(60) Provisional application No. 60/490,407, filed on Jul. 25, 2003.

(51) Int. Cl.
*A61F 13/02*    (2006.01)
(52) U.S. Cl.
USPC .......................................... 424/448; 424/449
(58) Field of Classification Search
USPC .......................................... 424/448, 449, 464
See application file for complete search history.

(56) References Cited

U.S. PATENT DOCUMENTS

| | | | |
|---|---|---|---|
| 4,058,599 | A | 11/1977 | Bauer et al. |
| 5,075,341 | A | 12/1991 | Mendelson et al. |
| 5,272,149 | A | 12/1993 | Stalling |
| 5,618,555 | A | 4/1997 | Tokuda et al. |
| 5,968,547 | A | 10/1999 | Reder et al. |
| 7,270,830 | B2 | 9/2007 | Reidenberg et al. |
| 2001/0002259 | A1 | 5/2001 | Reder et al. |
| 2003/0114475 | A1 | 6/2003 | Fox et al. |

FOREIGN PATENT DOCUMENTS

| | | |
|---|---|---|
| EP | 0430019 | 6/1991 |
| EP | 0432945 | 6/1991 |
| EP | 432945 A1 * | 6/1991 |
| EP | 0821957 | 2/1998 |
| JP | 04-128231 | 4/1992 |
| JP | 06-183956 | 5/1994 |
| JP | 07-304672 | 11/1995 |
| NZ | 539936 | 7/2004 |
| WO | WO-00/35456 | 6/2000 |
| WO | WO-03/079945 | 10/2003 |
| WO | 2004/054553 A1 | 7/2004 |
| WO | WO-2004/103317 | 12/2004 |
| WO | WO-2005/011579 | 2/2005 |

OTHER PUBLICATIONS

Fischer et al. Treatment of opiod-dependent pregnant women with buprenorphine, 2000, Addiction, 95 (2), 239-244.*
Lintzeris et al. Buprenorphine dosing regimen for inpatient heroin withdrawal: a symptom-triggered dose titration study, Jan. 2003, Drug and Alcohol Dependence, 70, 287-294.*
Montoya et al (Randomized Trial of Buprenorphine for Treatment of Concurrent Opiate and Cocaine Dependence; Clin Pharmacol Ther, Jan. 2004, vol. 75, (1). pp. 34-48).*
Fischer et al (Treatment of opioid-dependent pregnant woman with buprenorphine; Addition (2000) 95(2), 233-244).*
Reidenberg et al., "Physiologic Effects of Buprenorphine Transdermal System (BTDS) Dose Escalation in the Young, Healthy Elderly and Elderly Hypertensive Subjects," BIOSIS, Mar. 7. 2001XP002389136, Meeting Abstract.
Eder et al., "Buprenorphin in der Schwangerschaft," Psychiat PRAX, vol. 28, pp. 267-269, XP009068360 (2001).
Fisher et al., "Treatment of Opioid-Dependent Pregnant Women with Buprenorphine," Addiction, vol. 95, No. 2, pp. 239-244, XP002387913 (2000).
Stinchcomb et al., "Permeation of Buprenorphinie and its 3-Alkyl-Ester Prodrugs Through Human Skin," Pharmaceutical Research, vol. 13, No. 10, pp. 1519-1523, XP008016388, Oct. 1996.
Lainer et. al: "Evaluation of a Transdermal Buprenorphine Formulation in Opioid Detoxification" Tthe Authors Journal Compiliation 2007 Society for the Study of Addiction. vol. 102, pp. 1648-1656.
Lanier et al.: "Opioid Detoxification via single 7-day Application of a Buprenorphine Transdermal Patch: an Open-Label Evaluation" Psychopharmacology (2008) 198: 149-158.
A Japanese Office Action dated Jun. 11, 2013 issued in Japanese Application No. 2006-521307, the Japanese national phase of PCT/US2004/024010, of which the present application is the US national phase. Translation provided to Application by its agent in Japan.
A European Office Action dated Nov. 10, 2006 issued in European application No. 04779186.8, the European national phase of PCT/US2004/024010, of which the present application is the US national phase.

(Continued)

Primary Examiner — Michael G Hartley
Assistant Examiner — Micah-Paul Young
(74) Attorney, Agent, or Firm — Troutman Sanders LLP

(57) ABSTRACT

Dosage regimens of buprenorphine to treat withdrawal or abstinence syndrome in a drug dependent or opioid tolerant patient who is pregnant are described. The method includes treating withdrawal or abstinence syndrome of the patient by transdermal administration of an amount of buprenorphine effective to reduce withdrawal symptoms. For example, a first buprenorphine-containing transdermal dosage form can be administered for a first dosing period that is no more than about 5 days; a second buprenorphine-containing transdermal dosage form for a second dosing period that is no more than about 5 days, the second dosage form comprising the same or a greater dosage of buprenorphine than the first dosage form; and a third buprenorphine-containing transdermal dosage form for a third dosing period that is at least 2 days, the third dosage form comprising the same or a greater dosage of buprenorphine than the second dosage form.

11 Claims, No Drawings

(56) References Cited

OTHER PUBLICATIONS

An Australian Office Action dated May 4, 2007 issued in Australian application No. 2004261182, the Australian national phase of PCT/US2004/024010, of which the present application is the US national phase.

A Canadian Office Action dated Jan. 28, 2009 issued in Canadian application No. 2,530,005, the Canadian national phase of PCT/US2004/024010, of which the present application is the US national phase.

A Chinese Office Action dated Aug. 17, 2007 issued in Chinese Application No. 200480021563.3, the Chinese national phase of PCT/US2004/024010, of which the present application is the US national phase. Translation provided to Applicant by its agent in China.

An Eurasian Office Action dated Dec. 21, 2006 issued in Eurasian Application No. 200600200, the Eurasian national phase of PCT/US2004/024010, of which the present application is the US national phase. Translation provided to Applicant by its agent in Eurasia.

A Georgian Search Report dated May 24, 2010 issued in Georgian application No. 2004009184, the Georgian national phase of PCT/US2004/024010, of which the present application is the US national phase.

A Japanese Office Action dated Aug. 3, 2010 issued in Japanese Application No. 2006-521307, the Japanese national phase of PCT/US2004/024010, of which the present application is the US national phase.

A Japanese Office Action dated Apr. 19, 2011 issued in Japanese Application No. 2006-521307, the Japanese national phase of PCT/US2004/024010, of which the present application is the US national phase.

A Japanese Inquiry from the Board of Appeal dated Feb. 19, 2013 issued in Japanese Application No. 2006-521307, the Japanese national phase of PCT1US20041024010, of which the present application is the US national phase.

A Korean Office Action dated Jun. 26, 2007 issued in Korean Application No. 10-2006-7001688, the Korean national phase of PCT/US2004/024010, of which the present application is the US national phase.

A Korean Office Action dated Dec. 27, 2007 issued in Korean Application No. 10-2006-7001688, the Korean national phase of PCT/US2004/024010, of which the present application is the US national phase.

A New Zealand Office Action dated Jul. 18, 2008 issued in New Zealand application No. 545505, the New Zealand national phase of PCT/US2004/024010, of which the present application is the US national phase.

A Ukrainian Office Action dated Jul. 26, 2004 issued in Ukrainian application No. a200602136, the Ukrainian national phase of PCT/US20041024010, of which the present application is the US national phase.

A Norwegian Office Action dated Mar. 27, 2012 issued in Norwegian Application No. 20060913, the Norwegian national phase of PCT/US2004/024010, of which the present application is the US national phase.

Frederiksen, Marilynn. "Physiologic Changes in Pregnancy: Effect on Drug Disposition" Posted Jan. 31, 2001: http://www.fda.gov/cder/present/clinpharm2000/Frederiksen/.

Lintzeris et al.,"Buprenorphine dosing regime for inpatient heroin withdrawal: a system triggered dose titration study." Drug and Alcohol Dependence vol. 70(3), pp. 287-294 (Jun. 2003).

\* cited by examiner

TREATMENT OF DEPENDENCE WITHDRAWAL

CROSS REFERENCE TO PRIOR APPLICATION

This is a U.S. national phase application under 35 U.S.C. §371 of International Patent Application No. PCT/US2004/024010 filed Jul. 26, 2004, and claims benefit of U.S. Provisional Application Ser. No. 60/490,407 filed Jul. 25, 2003, which is incorporated by reference herein. The International Application was published in English on Feb. 10, 2005 as WO 2005/011579 A2 under PCT Article 21(2).

FIELD OF THE INVENTION

The present invention relates to the treatment of withdrawal symptoms. In particular, the invention relates to treating withdrawal in pregnant women dependent upon opioids, and to treatment of opioid dependence in the newborn.

BACKGROUND OF THE INVENTION

Opiate withdrawal, or abstinence, syndrome is the constellation of dilated pupils, coryza (runny nose), irritability, nausea and/or vomiting and/or diarrhea, and piloerection (goose flesh) in the setting of decrease or absence of opioid dosing or during the introduction of an opioid antagonist (e.g. naloxone or naltrexone). This syndrome is often associated with opioid addiction, because many addicts cannot maintain their supply of opioids and do not de-escalate their dosing prior to running out of drug. However the presence of an abstinence syndrome is not the most essential component of addiction, as addiction is "a behavioral pattern characterized by compulsive use of a drug and overwhelming involvement with its procurement and use" despite known harmful effects (Goodman & Gillman's The Pharmacological Basis of Therapeutics, J. G. Hardman (Ed.), McGraw-Hill Professional Publishing, 2001, p. 586). One part of potential treatment of addiction is the management of opioid abstinence syndrome. Opioid addicts can be very tolerant to opioids and therefore suffer severe and/or prolonged abstinence syndrome when they attempt to stop their self destructive behavior. Many medications have been utilized to decrease or prevent opioid abstinence syndrome beginning with methadone in the 1970s. In addition some medications have been studied to decrease the opioid "hunger" of addicts. These medications are considered treatment for opioid addiction.

At present, there are many medications being tested to treat opioid addiction, for example: Abbott 69024, Amantidine, Bupropion, Bromocriptine, Buspirone, Carbamazepine (Tegretol), Fluoxetine (Prozac), Flupenthixol, Gepirone, LAAM, Mazindol, Naltrexone and Schering 23390 (see ref: Scientific American, March 1991, pp. 94-103). Very few of these drugs have proven effective. New drugs are aimed at replacing methadone for opioid dependence, such as buprenorphine, however, only limited clinical study information is available (Fudula et al., NIDA Research Monograph 1991, 105:587-588).

Continuous opioid abuse during pregnancy has particular importance, as this can lead to complications in the mother and her baby. It is a recommended practice to maintain opioid-dependence in pregnant women with synthetic opioids. According to international guidelines, methadone is the recommended substance. However, a neonatal abstinence syndrome (NAS) is observed in 60-80% of neonates having a longer duration, but less severity, in comparison to NAS after heroin consumption during pregnancy (Eder et al., Psychiatr Prax 2001, 28:267-69). NAS may be characterized by one or more of the following: tremor, irritability, hypertonicity, vomiting, sneezing, fever, poor suckling, and convulsions.

Recent studies have investigated the safety and efficacy of other synthetic opioids, including sublingual buprenorphine, for the treatment of pregnant patients. Maintenance therapy with buprenorphine has proven safety and efficacy during pregnancy, where the mother was free of continuous heroin abuse, as verified through supervised urine-toxicology (Eder et al., Psychiatr Prax 2001, 28:267-69).

Buprenorphine is a potent, partial agonist of the µ-opioid receptor that has been shown to be effective to control pain in a wide range of patients when delivered by a number of different routes of administration, including intravenously, epidurally, intrathecally, or sublingually in both young and elderly patients (Inagaki et al., Anesth Analg 1996, 83:530-536; Brema et al., Int J Clin Pharmacol Res 1996, 16:109-116; Capogna et al., Anaesthesia 1988, 43:128-130; Adrianensen et al., Acta Anaesthesiol Belg 1985, 36:33-40; Tauzin-Fin et al., Eur J Anaesthesiol 1998, 15:147-152; Nasar et al., Curr Med Res Opin 1986, 10:251-255). There are several types of transdermal formulations of buprenorphine reported in the literature. See, for example, U.S. Pat. No. 5,240,711 to Hille et al., U.S. Pat. No. 5,225,199 to Hidaka et al., U.S. Pat. No. 5,069,909 to Sharma et al., U.S. Pat. No. 4,806,341 to Chien et al.; U.S. Pat. No. 5,026,556 to Drust et al.; U.S. Pat. No. 5,613,958 to Kochinke et al.; and U.S. Pat. No. 5,968,547 to Reder et al. Transdermal delivery systems of buprenorphine, made by Lohmann Therapie-Systeme GmbH & Co., are currently sold in the European Union under the trademark name TRANSTEC®. These patches contain 20, 30, and 40 mg of buprenorphine, with an approximate delivery or "flux" rate of 35, 52.5, and 70 µg/hr, respectively. Transdermal delivery systems of fentanyl, another opioid antagonist, are commercially available, e.g., under the name Duralgesic.

Buprenorphine has been shown in humans to be a potent opioid antagonist analgesic not displaying the psychotomimetic effects sometimes found with other antagonist analgesics. In animal and human tests, buprenorphine has been shown to have both agonist (morphine-like) and (morphine) antagonist properties. However from direct dependence studies in animals and in humans it has been concluded that buprenorphine does not produce significant physical dependence and the potential to produce psychological dependence is low as indicated by animal self administration studies and by the measurement of euphorigenic effects in human post addicts. In humans the agonist and narcotic antagonist characteristics of buprenorphine have been demonstrated in opiate addicts. Thus oral buprenorphine in the dose range 6-16 mg has been shown to precipitate abstinence in highly dependent opiate addicts presenting for detoxification. On the other hand in a study involving subjects stabilized on a relatively low daily dose of oral methadone, sublingual buprenorphine could be substituted for methadone with only a low level of discomfort. In this situation buprenorphine was behaving as an opiate agonist of low intrinsic activity.

A recent study has assessed the outcome of drug dependent mothers and influence of buprenorphine maintenance on neonatal morbidity (Jernite et al., Arch. Pediatr., 1999, 6(11): 1179-85). This study showed that the use of buprenorphine during pregnancy may reduce dependence complications in the fetus/infant such as prematurity, growth retardation, fetal distress and fetal death.

The consequences of active opioid abuse to the fetus in the pregnant addict include: decreased oxygenation resulting in damage to multiple organs due to respiratory depression in the mother; malnutrition in utero due to maternal malnutrition from opiate induced inanition or confusion; abnormal neural development due to opiate exposure during development resulting in down regulation of opiate receptors and alternate abnormal neural pathway development; exposure to other fetal toxins, since most illegally obtained opiates are contaminated; exposure to other fetal toxins due to impaired judgment of the opiate intoxicated mother; and exposure to trauma (intentional and accidental) due to impaired judgment of the opiate intoxicated mother.

Information on the direct and indirect effects of buprenorphine on the fetus is essential for determining its potential for treatment of the pregnant opiate addict. In addition, therapeutic levels of buprenorphine in maternal circulation may have no indirect effects (via the placenta) on the fetus (Nanovskaya et al., J. Pharmacology and Exp. Ther. 2002, 300:26-33). This study observed that low transplacental transfer of buprenorphine to the fetal circuit may explain the moderate/absence of neonatal withdrawal in the limited number of reports on mothers treated with the drug during pregnancy. Furthermore, buprenorphine treatment appears to be well accepted by pregnant mothers, compared to methadone treatment, as demonstrated by compliance with therapy (Fischer et al., Addiction 2000, 95(2):239-244). Current buprenorphine treatment for addiction prevents and treats abstinence syndrome and may decrease opioid "hunger." Buprenorphine for opioid addiction is delivered via daily or alternate day sublingual tablets or sublingual solution.

While methadone is the only opioid against currently approved in the US for maintenance therapy, buprenorphine has many of the desired characteristics of a treatment for opiate dependence: (a) the ability to substitute for opiates in moderately dependent individuals; (b) very mild abstinence effects when the drug is withdrawn; and (c) very good safety.

For maintenance treatment, however, there are potential problems of a sublingual buprenorphine product for the treatment of opiate addicts, such as the requirement for frequent dosing. This limits the mobility of the addict during treatment and often produces a perception that returning to a productive life will be difficult due to scheduling supervised dosing.

Thus, the lack of effective therapies for the treatment of drug dependence for both the general population and specifically drug dependent pregnant woman strongly suggests that novel approaches are needed. The present invention is directed to meeting this and other needs, and provides a method directed to the prevention and/or treatment of abstinence syndrome in opioid dependent pregnant women and their fetuses.

SUMMARY OF THE INVENTION

The present invention provides a specific regimen of buprenorphine that enables treatment of withdrawal or abstinence syndrome in a drug dependent or opioid tolerant patient in need of such treatment.

The Invention provides a method of treating withdrawal or abstinence syndrome in a drug dependent or opioid tolerant patient in need of such treatment, which methods comprises transdermal administration of an amount of buprenorphine effective to reduce withdrawal symptoms in the patient. Preferably, the patient is a pregnant woman. The women can be addicted to, for example, an opiate such as, e.g., heroin.

The invention also provides a method of treating withdrawal or abstinence syndrome in a patient comprising administering to the patient (1) a first buprenorphine-containing transdermal dosage form for a first dosing period that is no more than about S days; (2) a second buprenorphine-containing transdermal dosage form for a second dosing period that is no more than about 5 days, the second dosage form comprising the same dosage of buprenorphine as greater dosage of buprenorphine than, the first dosage form; and (3) a third buprenorphrine-containing transdermal dosage form for a third dosing period for at least 2 days, the third dosage form comprising a greater dosage of buprenorphine than the second dosage form.

In specific embodiments, the first, second, and third transdermal dosage forms, respectively contain approximately the amounts of buprenorphine set forth in a row of the following table:

| First (mg) | Second (mg) | Third (mg) |
|---|---|---|
| 5 | 5 | 10 |
| 5 | 10 | 10 |
| 5 | 10 | 20 |
| 10 | 10 | 20 |
| 10 | 20 | 20 |

Preferably, the dosing regimen results in a plasma buprenorphine profile wherein the mean plasma buprenorphine concentration after the third dosage form is about 800 pg/ml.

In a preferred embodiment, the method of the invention further comprises administering a fourth buprenorphine-containing transdermal dosage form for a fourth dosing period after the third dosing period. For example, the fourth dosage form may comprise, for example, 10, 20, 30, or 40 mg of buprenorphine for a dosing period of 7 days.

In particular embodiments, the dosage forms are tapered down in dosage amounts once symptoms of withdrawal dissipate.

The transdermal administration can be produced by a transdermal system selected from a topical gel, a lotion, an ointment, a transmucosal system, a transmucosal device, and an iontophoretic delivery system.

DETAILED DESCRIPTION OF THE INVENTION

The present invention provides a method of more quickly achieving effective treatment and/or prevention of abstinence syndrome in a subject in need thereof. In a preferred embodiment, the method is applied to treating an opioid-dependent pregnant woman and reduces the abstinence syndrome in the newborn of the treated mother. Thus, the method of the invention can be applied to treat or prevent withdrawal from, e.g., heroin, in a pregnant woman. A pregnant woman to be treated according to the invention can be a woman dependent on a prescription or non-prescription drug before getting pregnant, or a woman becoming dependent during pregnancy.

The method comprises administering to the subject an effective amount of buprenorphine in a specific dosage form and regimen. This dosage form and regimen involves administering to the subject a series of transdermal dosage forms with incrementally increasing dosages of buprenorphine. Preferably, He dosage increase is rapid so as to achieve efficacy in as short a time as possible, while minimizing adverse effects of too high an initial dose of buprenorphine.

The transdermal dosage regimen of the invention provides a more effective method of administering buprenorphine for the treatment of dependence. If administered to a pregnant woman, the present method reduces the development of abstinence in the fetus (and later in the newborn) while treating the pregnant mother for drug dependence. In addition, the method does not require daily supervised dosing. Therefore, the method increases the degree of patient compliance with drug therapy and treatment efficacy. Indeed, in certain embodiments, the present invention advantageously achieves increased efficacy of control of withdrawal in both the pregnant woman, the fetus, and the newborn after delivery.

The dosage regimen of the present invention may alternatively be described in terms of administration of a series of transdermal dosage forms comprising incremental dosage increases of buprenorphine. This refers to the application of transdermal dosage forms to an addicted subject, preferably a pregnant woman, which can result in more rapidly achieving a blood level of buprenorphine sufficient to prevent and/or treat the patient's abstinence syndrome. The treatment would be maintained until such time as the patient was deemed ready for down-titration. The down-titration would not normally be initiated during a pregnancy, since there is risk of relapse to active addiction, which would pose a danger to the unborn child.

For example, a series of transdermal dosage forms may be administered in the dosage regimen, wherein the first dosage form contains 5 mg buprenorphine, followed by two subsequent 5 mg and 10 mg dosage forms. Alternatively, the dosage forms may include 10 mg and 10 mg buprenorphine, or 20 mg buprenorphine. In particular embodiments, 30 mg and/or 40 mg buprenorphine dosage levels are used.

As used herein, "BTDS" means "Buprenorphine Transdermal System", and "BTDS X", wherein "X" is a number higher than zero, means a transdermal dosage form containing X milligrams of buprenorphine. Thus, "BTDS 5" contains about 5 mg buprenorphine. Preferably, a BTDS contains buprenorphine in the form of a base or a salt, more preferably in the form of a base.

An "analgesically effective" amount of an analgesic agent means an amount of agent capable of lowering the level of pain experienced by a patient. The level of pain experienced by a patient can be assessed by use of a visual analog scale (VAS) or a Likert-type scale. A VAS is a straight line with one end of the line representing no pain and the other end of the line representing the worst imaginable pain. Patients are asked to mark on the line where they considered their pain to be at each time point, and the length from no pain to the mark can be related to the length of the full scale. A Likert-type scale is a rating scale, usually in the range of 1 to 5, based on degrees of agreement or disagreement to statements. A similar type of scale, although based on an 11 point scale (ranging from 0 to 10) can also be used. Such pain scales can be applied to visualize an alteration of the level of pain a patient experiences during treatment, e.g., a reduction of the level of pain a patient or a population of patients experiences before and after initiation of a pain therapy.

Buprenorphine

The present invention relates to buprenorphine or a pharmaceutically acceptable salt, ether derivative, ester derivative, acid derivative, enantiomer, diasteriomer, racemate, polymorph, or solvate thereof. Pharmacologically, without being bound to any particular theory, buprenorphine is considered in the art to be a partial agonist at μ opioid receptors in the central nervous system ("CNS") and peripheral tissues. Buprenorphine shares many of the actions, such as analgesia, of full μ opioid agonists. Partial agonists, generally, include compounds with affinity for a receptor, but unlike full agonists, elicit only a small degree of the pharmacological effect, even if a high proportion of receptors are occupied by the compound. A "ceiling effect" to analgesia (i.e., no additional analgesia with increasing dose) is well documented with respect to buprenorphine in many animal models. It is highly lipophilic and dissociates slowly from opioid receptors. It is further thought that buprenorphine binds with high affinity to μ and $κ_1$ receptors, and, with lower affinity, to δ receptors. The intrinsic agonist activity at the κ receptor seems to be limited and most evidence suggests that buprenorphine has antagonist activity at κ receptors. The lack of κ agonism accounts for buprenorphine's freedom from the dysphoric and psychotomrnimetic effects often seen with agonist/antagonist drugs. Other studies suggest that the opioid antagonist effects of buprenorphine may be mediated via an interaction with δ opioid receptors.

It is known in the art that buprenorphine binds slowly with, and dissociates slowly from, the μ receptor. The high affinity of buprenorphine for the μ receptor and its slow binding to, and dissociation from, the receptor is thought to possibly account for the prolonged duration of analgesia and, in part, for the limited physical dependence potential observed with the drug. The high affinity binding may also account for the fact that buprenorphine can block the μ agonist effects of other administered opioids.

Like other opioid agonists, buprenorphine produces dose-related analgesia. The exact mechanism has not been fully explained, but analgesia appears to result from a high affinity of buprenorphine for μ and possibly κ opioid receptors in the central nervous system. The drug may also alter the pain threshold (threshold of afferent nerve endings to noxious stimuli). On a weight basis, the analgesic potency of parenteral buprenorphine appears to be about 25 to about 50 times that of parenteral morphine, about 200 times that of pentazocine, and about 600 times that of meperidine.

Salts and Derivatives

Use of various pharmaceutically acceptable salts, ether derivatives, ester derivatives, acid derivatives, and aqueous solubility altering derivatives of the active compound also are encompassed by the present invention. The present invention further includes the use of all active individual enantiomers, diastereomers, racemates, and other isomers of the compound. The invention also includes the use of all polymorphs and solvates, such as hydrates and those formed with organic solvents, of this compound. Such isomers, polymorphs, and solvates may be prepared by methods known in the art, such as by regiospecific and/or enantioselective synthesis and resolution.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound.

The present invention includes prodrugs of the compound. Prodrugs include, but are not limited to, functional derivatives of buprenorphine that are readily convertible in vivo into buprenorphine. Conventional procedures for the selection and preparation of suitable prodrug derivatives are described, for example, in "Design of Prodrugs", ed. H. Bundgaard, Elsevier, 1985.

Transdermal Dosage Forms

Transdermal dosage forms are convenient dosage forms for delivering many different active therapeutically effective agents, including but not limited to analgesics, such as for example, opioid analgesics. Typical opioid analgesics include, but are not limited to, fentanyl, buprenorphine, etorphines, and other high potency narcotics. Transdermal dosage forms are particularly useful for timed release and sustained release of active agents.

Transdermal dosage forms may be classified into transdermal dosage articles and transdermal dosage compositions. The most common transdermal dosage article is a diffusion-driven transdermal system (transdermal patch) using either a fluid reservoir or a drug-in-adhesive matrix system. Transdermal dosage compositions include, but are not limited to, topical gels, lotions, ointments, transmucosal systems and devices, and iontophoretic (electrical diffusion) delivery systems. Preferably, the transdermal dosage form is a transdermal patch.

Transdermal patch dosage forms used in accordance with the invention preferably include a backing layer made of a pharmaceutically acceptable material which is impermeable to the buprenorphine. The backing layer preferably serves as a protective cover for the buprenorphine, and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties, and the like. Preferably, the materials used for the backing layer are laminates of such polymer films with a metal foil such as aluminum foil. The backing layer can be any appropriate thickness to provide the desired protective and support functions. A suitable thickness will be from about 10 to about 200 microns. Desirable materials and thickness will be apparent to the skilled artisan.

In certain preferred embodiments, the transdermal dosage forms used in accordance with the invention contain a pharmacologically or biologically acceptable polymer matrix layer. Generally, the polymers used to form the polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof. Exemplary materials for inclusion in the polymer matrix layer are silicone elastomers of the general polydimethylsiloxane structures, (e.g., silicone polymers). Preferred silicone polymers cross-link and are pharmaceutically or biologically acceptable. Other preferred materials for inclusion in the polymer matrix layer include: silicone polymers that are cross-linkable copolymers having dimethyl and/or dimethylvinyl siloxane units that can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable crosslinking agent. Suitable crosslinking agents include, e.g., tetrapropoxy silane. Preferred transdermal delivery systems used in accordance with the methods of the present invention include an adhesive layer to affix the dosage form to the skin of the patient for the desired period of administration. If the adhesive layer of the dosage form fails to provide adhesion for the desired period of time, it is possible to maintain contact between the dosage form with the skin by, for instance, affixing the dosage form to the skin of the patient with an adhesive tape, e.g., surgical tape.

The adhesive layer preferably includes using any adhesive known in the art that is pharmaceutically compatible with the dosage form and preferably hypoallergenic, such as polyacrylic adhesive polymers, acrylate copolymers (e.g. polyacrylate) and polyisobutylene adhesive polymers. In other preferred embodiments of the invention, the adhesive is a hypoallergenic and pressure-sensitive contact adhesive.

The transdermal dosage forms that can be used in accordance with the present invention may optionally include a permeation enhancing agent. Permeation enhancing agents are compounds that promote penetration and/or absorption of the buprenorphine through the skin and into the blood stream of the patient. A non-limiting list of permeation enhancing agents includes polyethylene glycols, surfactants, and the like.

Alternatively, permeation of buprenorphine may be enhanced by occlusion of the dosage form after application to the desired site on the patient with, e.g. an occlusive bandage. Permeation may also be enhanced by removing hair from the application site by, e.g. clipping, shaving or use of a depilatory agent. Another permeation enhancer is heat. It is thought that permeation can be enhanced by, among other things, the use of a radiating heat form, such as an infrared lamp, at the application site during application of the transdermal dosage form. Other means of enhancing permeation of buprenorphine, such as the use of iontophoretic means, are also contemplated to be within the scope of the present invention.

A preferred transdermal dosage form that may be used in accordance with the present invention includes a non-permeable backing layer made, for example, of polyester; an adhesive layer made, for example, of a polyacrylate, and a matrix containing the buprenorphine and other desirable pharmaceutical aids such as softeners, permeability enhancers, viscosity agents and the like.

The active agent, buprenorphine, may be included in the device in a drug reservoir, drug matrix or drug/adhesive layer. This area of the patch, and the amount of active agent per unit area determine the limit dose, as one of ordinary skill in the art can readily determine.

Certain preferred transdermal delivery systems also include a softening agent in the reservoir or matrix. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides, particularly medium-chain triglycerides of caprylic/capric acids or coconut oil. Further examples of suitable softeners are, for example, multivalent alcohols as glycerol and 1,2-propanediol, as well as softeners such as levulinic acid and caprylic acid, which can also be esterified by polyethylene glycols.

A buprenorphine solvent may also be included in the transdermal delivery systems of the present invention. Preferably, the solvent dissolves the buprenorphine to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable components that may be included in the reservoir or matrix include solvents, for example, alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective release layer. The removable protective layer is removed prior to application, and may consist of the material used for the backing layer described above, provided that it is rendered removable, for example, by a silicone treatment. Other removable protective layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage form used in accordance with the invention and the type of device used are not considered critical to the method of the invention, provided that the device delivers the active agent, e.g. buprenorphine, for the desired time period and at the desired flux rate, i.e., the rate or penetration of the active agent through the skin of an individual, of the transdermal dosage form.

Certain preferred transdermal dosage forms for use in accordance with the present invention are described in U.S. Pat. No. 5,240,711 to Hille, et. al.; (assigned to LTS Lohmann Therapie-Systeme GmbH & Co.), hereby incorporated by reference. Such buprenorphine transdermal delivery systems may be a laminated composite having an impermeable backing layer containing buprenorphine, and optionally, a permeation enhancer, and a pressure-sensitive adhesive. A preferred transdermal dosage form in accordance with the U.S. Pat. No. 5,240,711 includes: (i) a polyester backing layer which is impermeable to buprenorphine; (ii) a polyacrylate adhesive layer; (iii) a separating polyester layer; and (iv) a matrix containing buprenorphine or a salt thereof, a solvent for the buprenorphine, a softener and a polyacrylate adhesive. The buprenorphine solvent may or may not be present in the final formulation. Preferably, the matrix includes about 10 to about 95% (by weight) polymeric material, about 0.1 to about 40% (by weight) softener, and about 0.1 to about 30% (by weight) buprenorphine. A solvent for the buprenorphine base or pharmaceutically acceptable salt thereof may be included as about 0.1 to about 30% (by weight).

The dosage forms of the present invention may also include one or more inactivating agents. The term "inactivating agent" refers to a compound that inactivates or crosslinks the active agent, in order to decrease the abuse potential of the transdermal dosage form. Non-limiting examples of inactivating agents include, but are not limited to, polymerizing agents, photo-initiators, and formalin. Examples of crosslinking or polymerizing agents include diisocyanates, peroxides, diimides, diols, triols, epoxides, cyanoacrylates, and UV activated monomers.

Any appropriate additives, inactivating agents, and dosage forms that are known in the art may also be used in combination with the method of the invention.

In a preferred embodiment, the method of the present invention is used to treat withdrawal symptoms in the drug dependent pregnant woman. In another preferred embodiment, the method of the present invention is used to prevent withdrawal symptoms in the newborn by treatment of the dependent pregnant mother.

The method of the present invention preferably comprises administering buprenorphine in a manner that achieves a gradual increase in the plasma concentration of buprenorphine in the patient. In a preferred embodiment, the plasma profile achieved by the method of the present invention may be described as follows: the mean plasma buprenorphine concentration after initial titration administration with a two 20 mg buprenorphine patches, which results in approximately 800 pg/ml.

Topical preparations typically contain a suspending agent and optionally, an antifoaming agent. Such topical preparations may be liquid drenches, alcoholic solutions, topical cleansers, cleansing creams, skin gels, skin lotions, and shampoos in cream or gel formulations (including, but not limited to aqueous solutions and suspensions).

Alternatively, buprenorphine can be administered in the form of liposome delivery system, such as small unilamellar vesicles, large unilamellar vesicles and multilamellar vesicles that may be included in the transdermal article or transdermal composition. Liposomes can be formed from a variety of phospholipids, such as cholesterol, stearylamine or phosphatidylcholines.

The transdermal dosage form may be formulated by any method known in the art and may be administered as suggested. Such formulations are described in U.S. Pat. Nos. 4,806,341; 5,240,711; and 5,968,547.

Administration

The unit dosage forms of the present invention are administered to a patient, preferably a human being, suffering from, or preventing, opiate abstinence syndrome. In a preferred embodiment, the patient is a pregnant woman. The unit dosage forms of the present invention may be administered at the defined dosing regimen in order to achieve optimal activity while reducing the incidence of any potential toxicity. For example, the method involves administering to the patient an effective amount of buprenorphine in a dosage regimen comprising a series of transdermal dosage forms that provide a concentration of approximately 800 pg/ml of buprenorphine.

The dosing regimen of the present invention comprises several discrete dosing periods. A dosing period is the time during which one of the transdermal dosage forms in the series is administered to the patient, and the dosing regimen will consist of a separate dosing period for administration of each transdermal dosage form in the series. Thus, for example, the first transdermal dosage form in the series may be worn by the patient for up to 5, preferably about 2 consecutive days. Upon removal, the second dosage form may then be worn by the patient for another period, preferably up to 5 days, more preferably about 2 consecutive days, and thereafter, the third dosage form may be worn by the patient for at least another 2 days. In a preferred embodiment, the total treatment period of the dosing regimen is six days until the desired dose is attained. This dose can then be maintained indefinitely. If an increase in dosage is required, then the dosage may be increased at an appropriate interval, e.g., every three to seven days.

In a specific embodiment, the dosage regimen begins as soon as the potential for opiate abstinence syndrome is discovered. In one embodiment, the initial dosage form begins with 5 mg buprenorphine for 2 days, followed by 5 mg for 2 days, then 10 mg for at least 2 days, preferably no more than about 10 days, most preferably no more than about 7 days. In another embodiment, the regimen escalates on a Q2 ("two-day") schedule such that the patient is at 20 mg total at 6 days after initiation of the treatment. In still another embodiment, subsequent dosages may be administered, with either the same or higher doses of buprenorphine, as needed by the patient. If a target plasma level is attained with the initial combination of patches, the treatment regime can be continually administered for an indefinite period of time, changing patches with a frequency extending from about every 2 days to about every 7 days or weekly, as needed. In case a higher plasma level of buprenorphine is needed by the patient and approved by a physician of ordinary skill, this can be achieved by administering a single patch with a higher dose, or multiple patches which together comprise a higher dose. For example, 2-4 BTDS 20, or multiple BTDS 30 or 40, could be administered to the patient at the same time.

The dosage of buprenorphine may vary according to a variety of factors such as underlying disease states, the individual's condition, weight, and age. The dosage predefined interval or regimen is selected in accordance with a variety of factors including species, age, weight, and medical condition of the patient; the severity of the condition to be treated; the selected transdermal delivery system; and the particular form of buprenorphine used. A physician or veterinarian of ordinary skill will readily be able to determine and prescribe the effective amount of the drug required to prevent, counter or arrest the progress of the condition in view of this disclosure. Optimal precision in achieving concentrations of drug within the range that yields efficacy without toxicity requires a regimen based on the kinetics of the drug's availability to target sites. This involves a consideration of the absorption, distribution, metabolism, and excretion of a drug.

The composition or dosage form of the invention, when administered as a transdermal dosage form, may be provided to any body part as determined by one of ordinary skill in the art. For example, the composition or dosage form may be provided to the arm, trunk, back or chest of the patient. In the preferred embodiment for pregnant women, the placement is preferably on the upper arm or back. Repeated doses are preferably not administered to the same location each time, but to different locations. For example, each placement could be rotated to different areas, allowing 1 month to pass before utilizing the same location.

Generally, topical preparations contain from about 0.01 to about 100% by weight and preferably from about 3 to about 80% by weight of the compound, based upon 100% total weight of the topical preparation. Generally, transdermal dosage forms contain from about 0.01 to about 100% by weight and preferably from about 3 to about 50% by weight of the compound, based upon 100% total weight of the buprenorphine formulation in the dosage form.

The dosage forms used in the method of the present invention may be administered alone or in combination with other active agents. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. Alternatively, unit dosage forms of these various active agents may be independently optimized and combined to achieve a synergistic result wherein the pathology is reduced more than it would be if either active agent were used alone.

In an exemplary embodiment, the patients are pregnant female opiate addicts on stable methadone maintenance therapy. Each patient receives BTDS 5 for 3 days in addition to her usual methadone dose. On the $3^{rd}$ day after observing no difficulties, the physician removes her BTDS 5 and replaces it with BTDS 10 for 3 days while decreasing her methadone by 25%. On the $6^{th}$ day after observing no difficulties, her physician removes the BTDS 10 and replaces it with BTDS 20 for 3 days while decreasing her methadone by another 25%. On the $9^{th}$ day, after observing no difficulties, her physician adds a second BTDS 20 and decreases her methadone to 10% of the original dose. On the $11^{th}$ day, after observing no difficulties, the physician discontinues her methadone and manages her with two BTDS 20 s applied once a week for the remainder of the pregnancy. No preventive treatment of the baby is necessary.

Kits

The present invention also provides an embodiment wherein the components for practicing the invention can be conveniently provided in a kit form. In its simplest embodiment, a kit of the invention provides a set number of buprenorphine patches at set dosages, wherein the dosages are set according to the needs of the patient. A starter kit could, for example, provide dosages to escalate the total dosage up to 20 mg over a 6 day period. In a preferred embodiment, the kit will contain 2-5 mg, and 1-10 mg buprenorphine patches, totaling 20 mg over the 6 day period. A longer term kit will include the subsequent dosage patches, which may include the appropriate dosages to treat the particular patient. These may include 5, 10, 20, 30 or 40 mg patches. In a preferred embodiment, the kit will also contain patches to taper off the dosage regimen. Alternatively, a subsequent tapering off kit may be provided to lower the dosages prior to giving birth. Printed instructions on how to apply the patch, storage of the unit, and details of the treatment regimen are also included in all of the kits.

A kit of the invention preferably includes packaging and printed instructions for its use, e.g., on the packaging or package insert. The buprenorphine patches within the kit may be coded (i.e., color, numerical by day, or numerical by dose, etc.) for the patient. For example, the printed instructions may describe the use of the dosage regiment to treat or prevent diarrhea or other gastrointestinal conditions or disorders.

In a further embodiment, the kit will include a disposal container or device for disposal of used buprenorphine patches. Any such containers or devices known in the art can be used to prevent or limit potential abuse of the drug within the patch. As used herein, the term container has its broadest meaning, i.e., any receptacle for holding material.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that values are approximate, and are provided for description.

Patents, patent applications, publications, procedures, and the like are cited throughout this application, the disclosures of which are incorporated herein by reference in their entireties.

What is claimed is:

1. A method of treating withdrawal or abstinence syndrome in a drug dependent or opioid tolerant patient in need of such treatment, which method comprises transdermal administration by a buprenorphine-containing transdermal patch of an amount of buprenorphine effective to reduce withdrawal symptoms in the patient; and wherein the patient is a pregnant woman addicted to an opiate and the method comprises:
   (a) administering to the patient a first buprenorphine-containing transdermal patch for a first dosing period that is no longer than about 5 days;
   (b) administering to said patient a second buprenorphine-containing transdermal patch for a second dosing period that is no longer than about 5 days, wherein the second transdermal patch comprises the same dosage or a greater dosage of buprenorphine than the first transdermal patch; and
   (c) administering to the patient a third buprenorphine-containing transdermal patch for a third dosing period for at least 2 days, wherein the third transdermal patch comprises a greater dosage of buprenorphine than the second transdermal patch, and
   wherein the first, second, and third transdermal patches contain the amounts of buprenorphine selected from the group consisting of 5 mg, 5 mg, 10 mg; 5 mg, 10 mg, 10 mg; 5 mg, 10 mg, 20 mg; 10, mg, 10 mg, 20 mg; and 10 mg, 20 mg, 20 mg, respectively.

2. The method of claim 1, wherein the dosing regimen results in a plasma buprenorphine profile wherein the mean plasma buprenorphine concentration after administration of the third transdermal patch is about 800 pg/ml.

3. The method of claim 1, comprising administering to the patient one or more subsequent buprenorphine-containing transdermal patches, each for a subsequent dosing period, wherein the dose provided during each dosage period is one of the same, a higher or a lower dose than the preceding dose as needed by the patient to achieve desired relief from withdrawal or abstinence syndrome.

4. The method of claim 3, wherein each subsequent transdermal patch comprises a dose of 10 mg of buprenorphine, 20 mg of buprenorphine, 30 mg of buprenorphine, or 40 mg of buprenorphine.

5. The method of claim 3, wherein each subsequent transdermal patch is used for a dosing period of no more than 7 days.

6. The method of claim 3, wherein each subsequent transdermal patch comprises a lower dose of buprenorphine than the preceding transdermal patch, in order to taper down the dosage as symptoms of withdrawal or abstinence syndrome lessen or dissipate.

7. The method of claim 3, wherein administering the one or more subsequent transdermal patches results in a plasma buprenorphine profile wherein the mean plasma buprenorphine concentration is about 800 pg/ml.

8. The method of claim 3, wherein each subsequent transdermal patch is replaced at least once after 7 days.

9. The method of claim 3, wherein each subsequent transdermal patch is used for a dosing period of at least 2 days to not more than 7 days.

10. The method of claim 1, wherein the dosing regimen results in a plasma buprenorphine concentration after administration of the third transdermal patch of about 800 pg/ml.

11. The method of claim 3, wherein administering the one or more subsequent transdermal patches results in a plasma buprenorphine concentration of about 800 pg/ml.

* * * * *